(12) United States Patent
Taylor et al.

(10) Patent No.: US 7,378,094 B2
(45) Date of Patent: May 27, 2008

(54) THERAPEUTIC USES OF COMPLEMENT RECEPTOR 2

(75) Inventors: Ronald P. Taylor, Charlottesville, VA (US); Margaret A. Lindorfer, Charlottesville, VA (US); William M. Sutherland, Earlysville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 531 days.

(21) Appl. No.: 10/489,564

(22) PCT Filed: Aug. 28, 2002

(86) PCT No.: PCT/US02/28227

§ 371 (c)(1),
(2), (4) Date: Feb. 27, 2004

(87) PCT Pub. No.: WO03/018774

PCT Pub. Date: Mar. 6, 2003

(65) Prior Publication Data

US 2004/0191252 A1    Sep. 30, 2004

Related U.S. Application Data

(60) Provisional application No. 60/315,539, filed on Aug. 29, 2001, provisional application No. 60/388,355, filed on Jun. 13, 2002.

(51) Int. Cl.
*A61K 39/395* (2006.01)

(52) U.S. Cl. .............................. 424/133.1; 424/134.1; 424/138.1; 424/159.1; 424/164.1; 424/172.1; 530/387.3; 530/388.22; 530/399.3; 530/8.4; 530/388.8; 530/391.7

(58) Field of Classification Search ..................... None
See application file for complete search history.

(56) References Cited

U.S. PATENT DOCUMENTS

| 5,487,890 A | 1/1996 | Taylor et al. |
|---|---|---|
| 5,879,679 A | 3/1999 | Taylor et al. |
| 6,291,239 B1 | 9/2001 | Prodinger et al. |

OTHER PUBLICATIONS

Lindorfer, M. A., Jinivizian, H. B., Foley, P. L., Kennedy, A. D., Solga, M. D. and Taylor, R. P. (2003). "B Cell Complement Receptor 2 Transfer Reaction." Journal of Immunology, vol. 170, pp. 3671-3678.
Baiu, D. C., Prechl, J., Tchorbanov, A., Molina, H. D., Erdei, A., Sulica, A., Capel, P. J. A. and Hazenbos, W.L.W. (1999). "Modulation of the Humoral Immune Response by Antibody-Mediated Antigen Targenting to complement Receptors and Fc Receptors." Journal of Immunology, vol. 162, pp. 3125-3130.
Prechl, J., Tchorbanov, A., Horvath, A., Baiu, D. C., Hazenbos, W., Rajnavolgyi, E. Kurucz, I., Capel, P. J.A. and Erdei, A. (1999). "Targeting of influenza epitopes to murine CR1/CR2 using single-chain antibodies." Immunopharmacology, vol. 42, pp. 159-165.
Taylor, R. P., Nardin, A. and Sutherland, W. M. (1997). "Clearance of blood-borne pathogens mediated through bispecific monoclonal antibodies bound to the primate erythrocyte complement receptor." Cancer Immunol. Immunother, vol. 45, pp. 152-155.
Emlen, Woodruff, "Immune Complexes in Systemic Lupus Erythematosus," Dubois' Lupus Erythematosus, 4th ed., Daniel J. Wallace and Bevra Hannahs Hahn, eds., 1993, Chapter 11, pp. 100-107.
Salmon, J.E., "Abnormalities in Immune Complex Clearance and Fc Receptor Function," Dubois' Lupus Erythematosus, 4th ed., Daniel J. Wallace and Bevra Hannahs Hahn, eds., 1993, Chapter 12, pp. 108-119.
Whipple, E.C. et al., "Analysis of the In Vivo Trafficking of Stoichiometric Doses of an Anti-Complement Receptor 1/2 Monoclonal Antibody Infused Intravenously in Mice," J. Immunol. 2004, 173: 2297-2306.
Prechl, J. et al., "Targeting of Influenza Epitopes to Murine CR1/CR2 Using Single-Chain Antibodies," Immunopharmacology 42 (1999), 159-165.
Nolte, M.A., et al., "A Conduit System Distributes Chemokines and Small Blood-Borne Molecules Through the Splenic White Pulp," J. Exp. Med., vol. 198, No. 3, (2003) pp. 505-512.
Campbell, M.J. et al., "Idiotype Vaccination Against Murine B Cell Lymphoma," J. Immunol. (1987), vol. 139, No. 8, pp. 2825-2833.
Kanter, G., et al. "Cell-Free Production of scFv Fusion Proteins: An Efficient approach for Personalized Lymphoma Vaccines," Blood, Apr. 15, 2007, No. 109, No. 8, pp. 3393-3399.

*Primary Examiner*—David A. Saunders
*Assistant Examiner*—F. Pierre VanderVegt
(74) *Attorney, Agent, or Firm*—Barnes & Thornburg LLP

(57) ABSTRACT

The present invention is directed to an immune complex composition, and a method of using that complex to enhance an in viva immune response against a preselected target antigen. The immune complexes of the present invention comprise a monoclonal antibody specific for binding to complement receptor (CR2) site on B lymphocytes linked to a target antigen. As shown in FIG. 5A-5D immune complexes bound to monkey B cells are removed in concert with loss of CR2. FIGS. 5A and 5B demonstrate the % A1488 HB135 and % APhCy CD21 positive cells, out of the doubly positive FE CD20/PerCF CD45 population over time, after injection of A1488 labeled HB135 (an anti-CR2 antibody, administration indicated by first arrow) followed by injection of rabbit anti-mouse IgG (administration indicated by the second arrow). FIGS. 5C and 5D are plots of the molecules of equivalent soluble fluorochome (MESF) values for these populations.

15 Claims, 8 Drawing Sheets

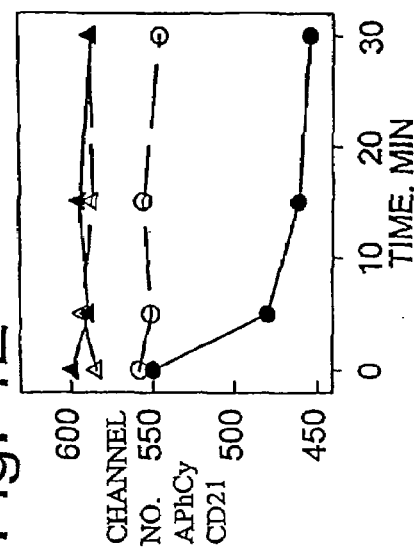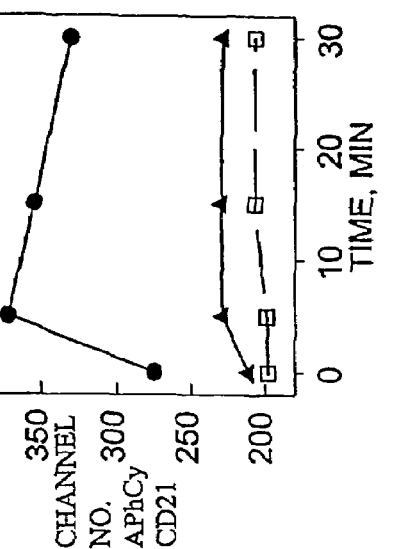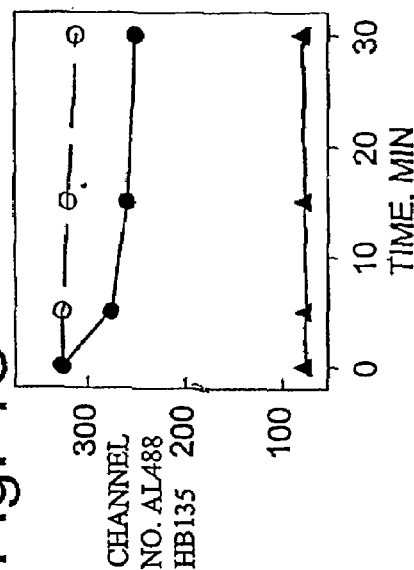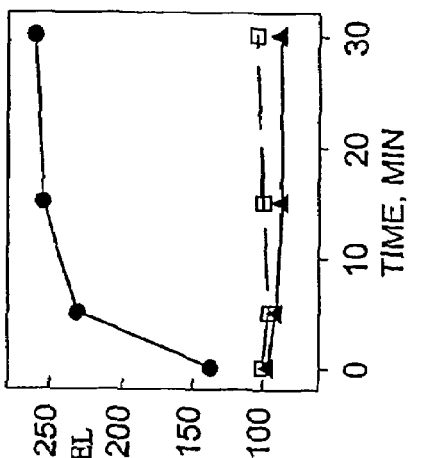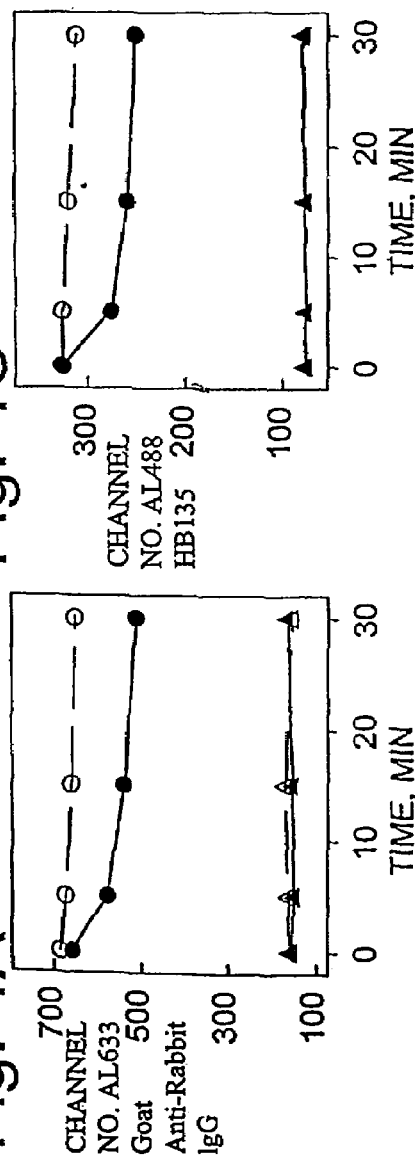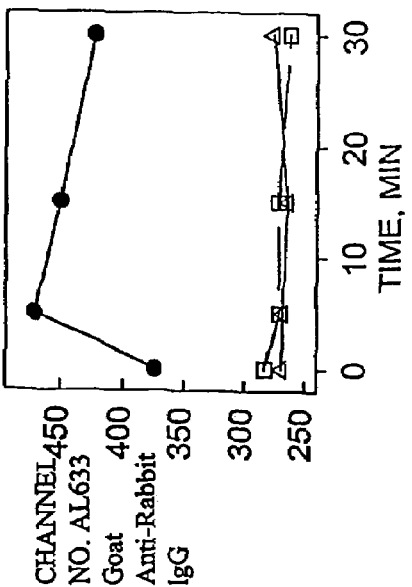

THERAPEUTIC USES OF COMPLEMENT RECEPTOR 2

RELATED APPLICATIONS

This application is a national stage filing of International Application No. PCT/US02/28227, filed Aug. 28, 2002, which claims priority under 35 U.S.C. § 119(e) to U.S. Provisional Patent Application Ser. Nos. 60/315,539, filed Aug. 29, 2001, 60/388,355, filed Jun. 13, 2002, the disclosures of which are incorporated herein by reference in their entirety.

US GOVERNMENT RIGHTS

This invention was made with United States Government support under Grant No. AR 43307, awarded by the National Institutes of Health. The United States Government has certain rights in the invention.

FIELD OF THE INVENTION

The present invention relates to bispecific monoclonal antibody complexes specific for both a unique receptor site (complement receptor 2) present on B lymphocytes (B-cell) and a preselected target antigen. The present invention further relates to methods for inducing an immune response against a specific antigen using the bispecific monoclonal antibody complexes of the present invention.

BACKGROUND OF THE INVENTION

Studies by several groups, initiated more than 30 years ago, revealed that immune complexes infused into animals are either rapidly phagocytosed by macrophages in the spleen and/or liver, or taken up by resident, but not antigen specific, B cells in the spleen and then later transferred to follicular dendritic cells (FDC). (Humphrey and Frank, Immunology, 13, 87-100 (1967); Brown et al., Immunology, 24, 955-968 (1973); Papamichail et al., Scandanavian Journal of Immunolgy, 4, 343-347 (1975); Klaus, Immunology, 34, 643-652 (1978); Humphrey et al., European Journal of Immunology, 14, 859-864, 1984; Heinen et al., European Journal of Immunolgy, 16, 167-172 (1986); van der Berg et al., European Journal of Immunolgy 22, 957-962 (1992)).

One component involved in the clearance of the infused immune complexes is the complement receptor 1 (CR1), present on primate erythrocytes. Research on the properties of CR1 has revealed that under a variety of conditions immune complexes (IC) comprising an antibody and antigen can be bound to this receptor either via complement opsonization or by the use of cross-linked complexes comprising monoclonal antibodies (mAbs) specific for CR1 itself (see U.S. Pat. Nos. 5,879,679 and 5,487,890, the disclosures of which are incorporated herein). Moreover, both in vivo and in vitro experiments have demonstrated that immune complexes bound to erythrocytes in either fashion are effectively transferred to acceptor macrophages in a reaction mediated by Fc receptors ("the transfer reaction"). During the transfer reaction CR1 is proteolyzed off of the erythrocytes, and then the entire immune complex and CR1 is internalized and destroyed by the acceptor macrophage. The key steps in the reaction include binding of the Fc regions of the antibodies in the immune complexes to Fc receptors on the macrophage, and then cleavage of CR1 by proteases associated with the macrophage, thus allowing the released immune complexes to be internalized by the macrophage.

These properties of primate erythrocyte CR1 have allowed the development of an invention comprising cross-linked mAb complexes for targeting circulating pathogens in the bloodstream. In particular, the cross-linked mAb complexes contain a mAb specific for erythrocyte CR1 cross linked with a mAb specific for a circulating pathogen. Pathogens present in the bloodstream become bound to such complexes upon administration of the complex to a patient, and the complexes themselves become bound to erythrocytes resulting in facilitated clearance of the pathogen via acceptor macrophages in the liver and spleen. The pathogen is then taken up by these acceptor cells and phagocytosed and destroyed, but the erythrocytes remain intact and are returned to the circulation.

Primate erythrocyte CR1 is similar in structure to complement receptor 2 protein (CR2), present on primate and non-primate B lymphocytes (B-cell). Both CR1 and CR2 are type I membrane-associated glycoproteins that are constructed with multiple copies of the short consensus repeat (SCR) folding motif, which is found in many complement control proteins. Both receptors have three separate domains: a cytoplasmic region, a transmembrane portion, and the main part of the protein, the extracytoplasmic domain, composed almost exclusively of multiple copies of the SCR.

Erythrocyte CR1 and B cell CR2 are both reduced in diseases, and in accordance with the present invention this is believed to result from the loss of the respective proteins during immune complex processing due to the transfer reaction. The immune complexes when bound to erythrocytes or B cells contain antigens, multiple copies of IgG, and either C3b when they are bound to erythrocytes, or C3dg or C3bi when they are bound to B cells. The fact that the complexes contain IgG allows them to interact with Fc receptors on the acceptor macrophages. Although the mechanism for antigen transfer from B cells to follicular dendritic cells (FDC) was never elucidated, it requires an intact complement system which promotes C3dg opsonization of the immune complexes.

As described in the present application, applicants have discovered that substrates bound to human B cells are capable of undergoing a CR2 mediated transfer reaction. This observation led to the present application, directed to bispecific reagents comprising a mAb specific for CR2 linked either directly or indirectly to a target antigen. The target antigen can be selected from any antigenic non-immunological component of a compound, cell or organism that one desires to effectively raise an immune response against or eliminate from the body of a vertebrate species. The bispecific antibody complexes of the present invention can be used to either present a particular antigen to a host organism's immune system, and thus induce a prophylactic immune response, or the bispecific antibody complex can be used to treat a pathogenic infection.

The bispecific antibody complexes of the present invention and their use in the present invention follows the natural mechanism for handling of immune complexed antigens which occurs in the body of warm-blooded vertebrates. In the natural process, complement labels the immune complex with C3dg, the immune complexes are then bound to B cell CR2, and finally transferred to FDC or macrophages. In the present invention, the monoclonal antibody specific for CR2 serves as a surrogate for C3dg and therefore insures efficient binding of substrates to B cell CR2, as well as later transfer of the antigen to the FDC. Under these conditions complement is not even required to achieve localization of the antigen to the FDC. The natural pathway is mediated by a reaction of highly variable efficiency: C3dg opsonization of immune complexed antigens. The present invention removes this uncertainty in antigen targeting, as the anti-CR2 mAb works far more effectively.

SUMMARY OF THE INVENTION

The present invention is directed to compositions and methods for treating a patient or non-diseased individual to generate a robust immune response to infectious agents or to other target antigens such as those found on cancer cells. More particularly, the composition comprises a bispecific antibody complex that includes a monoclonal antibody directed against complement receptor 2 (CR2) found on B cells and follicular dendritic cells and a second monoclonal antibody specific for the target antigen, wherein the monoclonal antibody and the target antigen are linked to one another.

TABLE I

Raji cell transfer substrates and probes

| Substrate | Probes* | |
|---|---|---|
| C3dg/A1488-PhiX174 | APhCy CD21 | |
| A1488-HB135 | APhCy CD21 | |
| A1488-HB135/RAMS | APhCy CD21 | A1633 GARB* |
| HB135/A1488-RAMS | APhCy CD21 | A1633 GARB* |
| HB135 | APhCy CD21 | A1488 RAMS* |
| F(ab)'$_2$-HB135 | | |
| HB135/A1488-RAMS | APhCy CD21 | |

*Samples probed with APhCy (allophycocyanin) CD21, A1633 goat anti-rabbit IgG (GARB) or A1488 rabbit anti-mouse IgG (RAMS) were blocked with mouse IgG, goat IgG or rabbit IgG, respectively FIG. 3A-D. Flow cytometry (fluorescence activated cell sorting) was used to measure the simultaneous transfer of an anti-CR2 monoclonal antibody (HB135) and CR2 from Raji cells to THP-1 cells. After 30 min, 73% of monoclonal antibody HB135 and 74% of CR2 were removed from Raji cells incubated with THP-1 cells, compared to 24% loss of monoclonal antibody HB 315 and 16% loss of CR2 from Raji cells incubated alone. Symbols: Filled circles, immune complex (A1488-HB135) opsonized Raji cells in the presence of THP-1 cells; open circles, immune complex opsonized Raji cells only; filled triangles, naïve Raji cells in the presence of THP-1 cells; open triangles, naïve Raji cells only; open squares, THP-1 cells only.

FIG. 4A-F. Flow cytometry (fluorescence activated cell sorting) was used to measure the simultaneous transfer of both components of an anti-CR2 monoclonal antibody based immune complex and CR2 from Raji cells to THP-1 cells. FIGS. 4A, 4C and 4E represent the loss of IC by Raji cells and FIGS. 4B, 4D and 4F represent the gain of IC by THP-1 cells. After 30 min, 58% of the immune complexes and 55% of CR2 were removed from Raji cells incubated with THP-1 cells, compared to 15% loss of immune complexes and 11% loss of CR2 from Raji cells incubated alone. The A1633 goat anti-rabbit IgG probe reported a 70% loss of immune complexes in the transfer sample. Symbols: Filled circles, immune complex (A1488-HB135/RAMS) opsonized Raji cells in the presence of THP-1 cells; open circles, immune complex opsonized Raji cells only; filled triangles, naïve Raji plus TIP-1 cells; open triangles, naïve Raji cells only; open squares, THP-1 cells only.

Figure 5A:
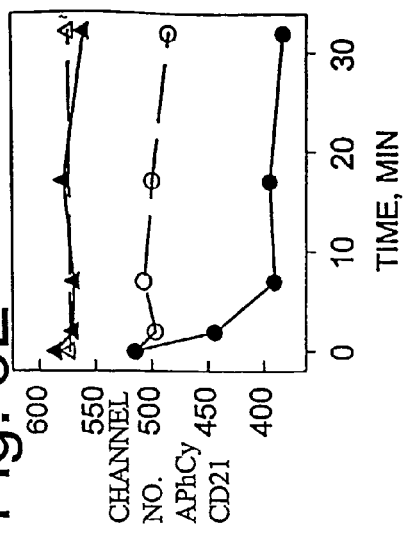
Figure 5C:
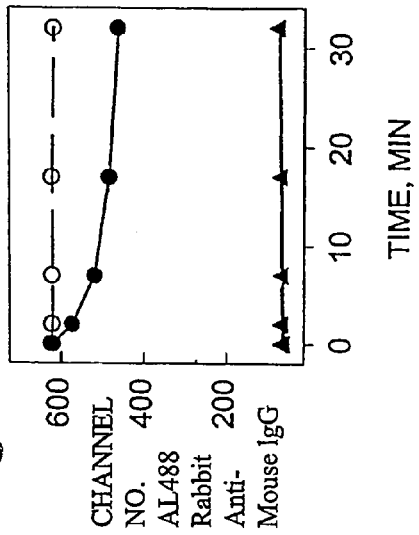
Figure 5E:
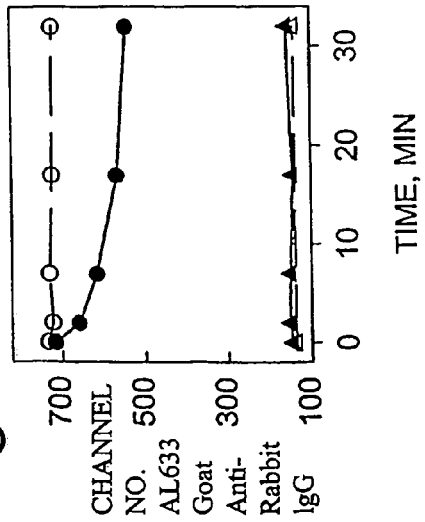
Figure 5B:
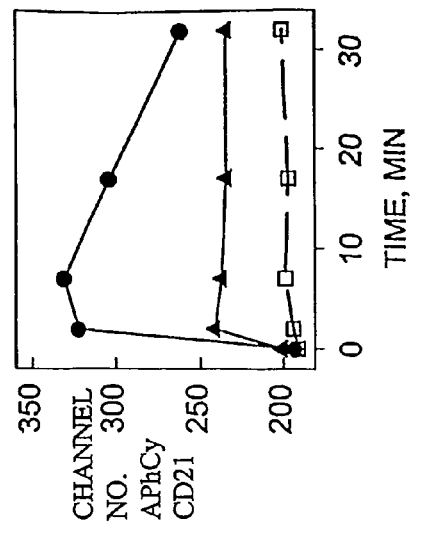
Figure 5D:
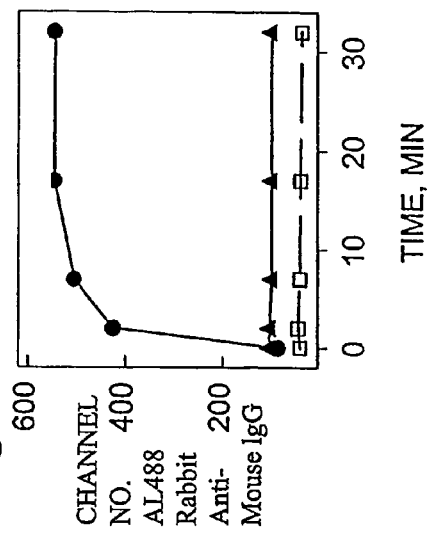
Figure 5F:
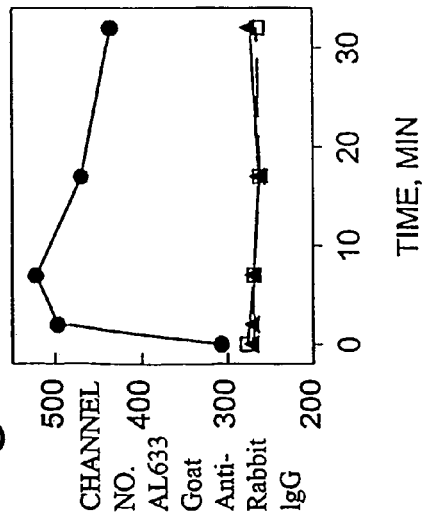

FIG. 5A-F. Flow cytometry (fluorescence activated cell sorting) was used to measure the simultaneous transfer of both components of an anti-CR2 monoclonal antibody based immune complex and CR2 from Raji cells to THP-1 cells. FIGS. 5A, 5C and 5E represent the loss of IC by Raji cells and FIGS. 5B, 5D and 5F represent the gain of IC by THP-1 cells After 30 min, 79% of the immune complexes and 67% of CR2 were removed from the Raji cells, compared to 8% loss of immune complexes and 23% loss of CR2 from Raji cells incubated alone. The A1633 goat anti-rabbit IgG probe also reported 75% loss of immune complexes for the transfer sample. Symbols: Filled circles, immune complex (HB135/A1488-RAMS) opsonized Raji cells in the presence of THP-1 cells; open circles, immune complex opsonized Raji cells only; filled triangles, naïve Raji plus THP-1 cells; open triangles, naïve Raji cells only; open squares, THP-1 cells only.

Figure 6A:
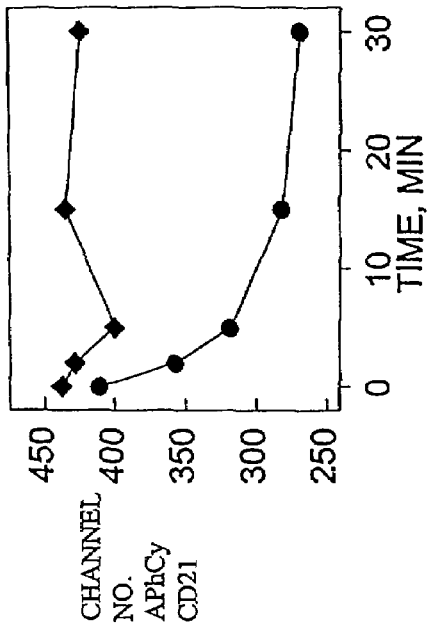
Figure 6C:
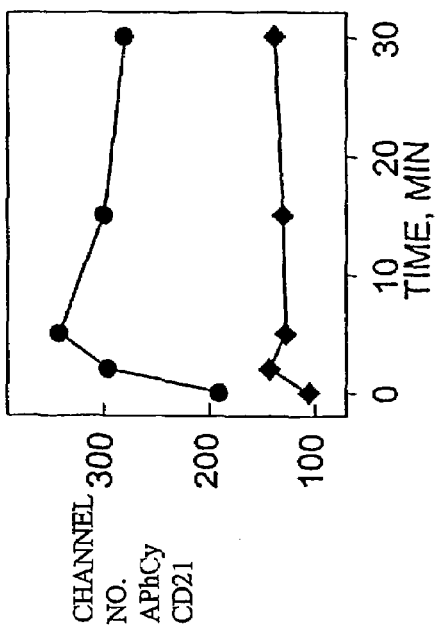
Figure 6B:
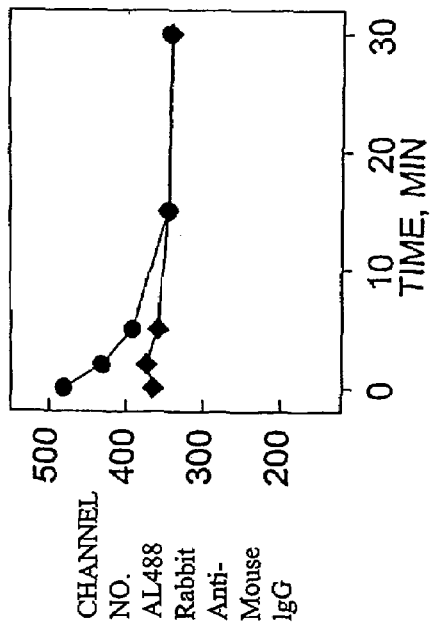
Figure 6D:
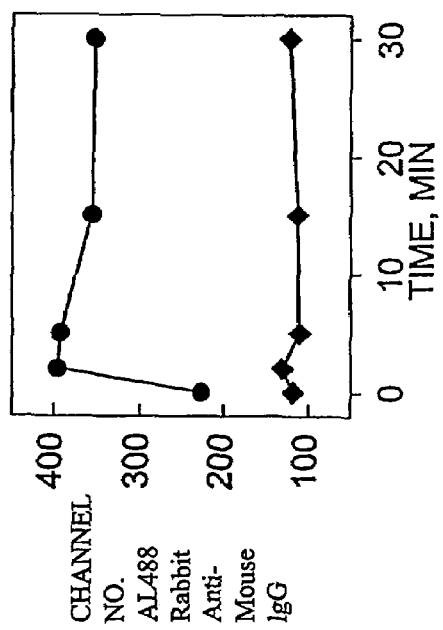

FIG. 6A-D. The Fc region of IgG is required for simultaneous transfer of anti-CR2 monoclonal antibody and CR2 from Raji cells to THP-1 cells. FIGS. 6A and 6C represent the loss of IC by Raji cells and FIGS. 6B and 6D represent the gain of IC by TJP-1 cells. After 30 min, 77% of monoclonal antibody HB135 and 72% of CR2 were removed from Raji cells ligated with monoclonal antibody HB135, compared to 27% loss of mnonoclonal antibody and 11% loss of CR2 from Raji cells with HB135 F(ab)'$_2$. The symbol ◆ represents Raji cells opsonized with the HB135 F(ab)'$_2$ and the symbol ● represents Raji cells opsonized with the intact HB135 mAb).

Figure 7A:
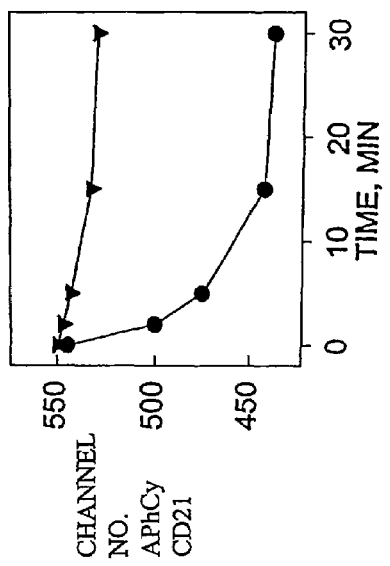
Figure 7C:
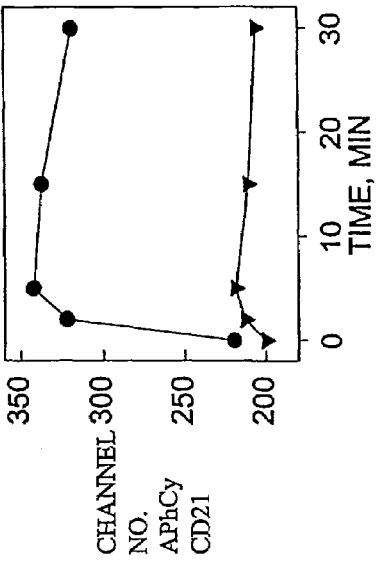
Figure 7B:
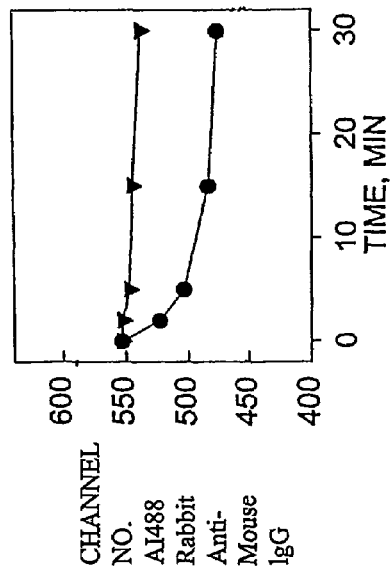
Figure 7D:
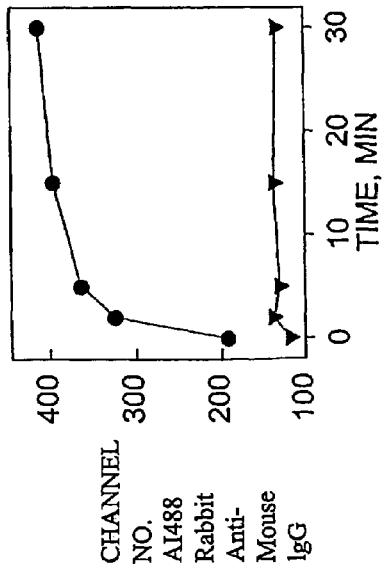

FIG. 7A-D. Pre-treatment of THP-1 cells with human IgG blocks transfer of an anti-CR2 monoclonal antibody based immune complex and CR2 from Raji cells to THP-1 cells. FIGS. 7A and 7C represent the loss of IC by Raji cells and FIGS. 7B and 7D represent the gain of IC by THP-1 cells After 30 min, 53% of the immune complexes and 61% of CR2 were removed from Raji cells incubated with THP-1 cells, while only 14% of the immune complexes and 17% of CR2 were removed from Raji cells incubated with THP-1 cells treated with 2 mg/ml human IgG. The symbol ▼ represents Raji cells opsonized with HB135/A1488RAMS IC and incubated with TBP-1 cells treated with Human IgG, and the symbol ● represents Raji cells opsonized with HB135/A1488RAMS and incubated with non-treated THP-1 cells.

FIG. 8. In vivo experiment demonstrating that immune complexes bound to monkey B cells are removed in concert with loss of CR2. A1488 monoclonal antibody HB 135 was infused i.v. into a monkey, and 1 h later rabbit anti-mouse IgG was infused. Infusions are denoted by arrows on the x-axis. Blood samples were processed and analyzed by flow cytometry. In FIGS. 8A and 8B are plotted the % A1488 HB135 and % APhCy CD21 positive cells, out of the doubly positive PE CD20/PerCP CD45 population. FIGS. 8C and 8D are plotted the molecules of equivalent soluble fluorochome (MESF) values for these populations. In vitro calibrations in which equivalent amounts of A1488 monoclonal antibody BB 135 were added to anti-coagulated whole blood (open circles) gave virtually identical binding to B cells.

DETAILED DESCRIPTION OF THE INVENTION

Definitions

In describing and claiming the invention, the following terminology will be used in accordance with the definitions set forth below.

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

The term "peptide" encompasses a sequence of 3 or more amino acids wherein the amino acids are naturally occurring or synthetic (non-naturally occurring) amino acids. Peptide mimetics include peptides having one or more of the following modifications:

1. peptides wherein one or more of the peptidyl —C(O)NR— linkages (bonds) have been replaced by a non-peptidyl linkage such as a —$CH_2$-carbamate linkage (—$CH_2$OC(O)NR—), a phosphonate linkage, a —$CH_2$-sulfonamide (—$CH_2$—S(O)$_2$NR—) linkage, a urea (—NHC(O)NH—) linkage, a —$CH_2$ -secondary amine linkage, or with an alkylated peptidyl linkage (—C(O)NR—) wherein R is $C_1$-$C_4$ alkyl;
2. peptides wherein the N-terminus is derivatized to a —NRR$_1$ group, to a —NRC(O)R group, to a —NRC(O)OR group, to a —NRS(O)$_2$R group, to a —NHC(O)NHR group where R and R$_1$ are hydrogen or $C_1$-$C_4$ alkyl with the proviso that R and R$_1$ are not both hydrogen;
3. peptides wherein the C terminus is derivatized to —C(O)R$_2$ where R$_2$ is selected from the group consisting of $C_1$-$C_4$ alkoxy, and —NR$_3$R$_4$ where R$_3$ and R$_4$ are independently selected from the group consisting of hydrogen and $C_1$-$C_4$ alkyl.

Naturally occurring amino acid residues in peptides are abbreviated as recommended by the IUPAC-IUB Biochemical Nomenclature Commission as follows: Phenylalanine is Phe or F; Leucine is Leu or L; Isoleucine is Ile or I; Methionine is Met or M; Norleucine is Nle; Valine is Vat or V; Serine is Ser or S; Proline is Pro or P; Threonine is Thr or T; Alanine is Ala or A; Tyrosine is Tyr or Y; Histidine is His or H; Glutamine is Gin or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and X is any amino acid. Other naturally occurring amino acids include, by way of example, 4-hydroxyproline, 5-hydroxylysine, and the like.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp As used herein, the term "purified" and like terms relate to the isolation of a molecule or compound in a form that is substantially free (i.e. at least 60% free, preferably 80% free, and most preferably greater than 90% free) from other components with which they are naturally associated.

As used herein, the term "treating" includes alleviating the symptoms associated with a specific disorder or condition and/or preventing or eliminating said symptoms. For example, treating cancer includes preventing or slowing the growth and/or division of cancer cells as well as killing cancer cells.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents and includes agents approved by a regulatory agency of the US Federal government or listed in the US Pharmacopeia for use in animals, including humans.

As used herein, the term "parenteral" includes administration subcutaneously, intravenously or intramuscularly.

The term "epitope" as used herein refers to the specific portion of an antigen which interacts with the complementarity determining region (CDR) of an antibody.

The term "complementary determining region" (CDR) as used herein refers to the hypervariable region of an antibody molecule that forms a surface complementary to the 3-dimensional surface of the antibody's corresponding antigen.

As used herein, two compounds are "linked" when they are chemical bound to one another either directly or indirectly through a linking moiety.

As used herein, the term "target antigen" refers to a compound, or fragment thereof, that is antigenic (i.e. capable of eliciting an immune response in a mammal) and directly related to a specific causative agent of disease. Examples of such target antigens include unique protein and carbohydrate antigens presented by pathogenic organisms or cancer cells as well as toxins and poisons. Target antigens do not include components of a normal healthy immune system or the complement cascade.

As used herein, the term "normal healthy immune system" refers to the various inmmune system components that are found in a typical warm blooded vertebrate species that is free of disease. More particularly, excluded from a normal healthy immune system are cells of the immune system that divide or express gene products at uncharacteristic rates (e.g. cancer cells), as well as antigens that are overexpressed on such cells.

The Invention

The present invention is based on the unique structural and biophysical properties of the cell complement receptor 2 (CR2) found on B cells and dendritic cells. More specifically, applicants have discovered that substrates that are bound to CR2 of primate B cells are transferred to follicular dendritic cells (FDC) or acceptor macrophages in a reaction mediated by Fc receptors ("The Transfer Reaction"). During the transfer reaction CR2 is proteolyzed off of the B cell or dendritic cell, and the entire immune complex, including CR2 is transferred to follicular dendritic cells or acceptor macrophages. The present invention is directed to novel complexes and methods that utilize the CR2 transfer reaction mechanism to induce or enhance an immune response against a specific antigen.

In accordance with one embodiment a novel immune complex is provided comprising a target antigen that is linked, covalently or non-covalently, to a monoclonal antibody wherein the monoclonal antibody is specific for CR2. The target antigen can be linked to the CR2 monoclonal antibody either directly or indirectly through a linker. In one embodiment the linker constitutes a second monoclonal antibody that specifically binds to the target antigen. One important feature of the novel immune complexes of the present invention is that they contain one or more antibody constant fragments (Fc), thus allowing the complex to take part in the CR2 transfer reaction after binding of the complex to B cell CR2. The present invention also encompasses pharmaceutical compositions wherein the composition comprises a bispecific monoclonal antibody complex of the present invention in combination with a pharmaceutically acceptable carrier.

In accordance with the present invention these novel immune complexes will be administered to a warm blooded vertebrate to initiate the transfer reaction and move the antigen from the B cell to the follicular dendritic cell. As shown in Example 4, localization of CR2-associated IC (prepared with the anti-CR2 monoclonal antibody) to the spleen in the monkey model closely simulates the important and natural process of immune complex processing as described above. Applicant's in vitro studies demonstrate that such a transfer can occur between donor Raji cells and acceptor macrophages, in a reaction mediated by Fc receptors (FcR). The identity of other cells which remove immune complexes and associated B cell CR2 remains to be defined, but FDC (found in the spleen and lymphatic tissue), which have high levels of FcγRII as well as CR2, are the most likely candidates. As stated by Humphrey (1984, see above) "Why and how B lymphocytes with CR1 and CR2 receptors should transfer immune complexes containing complement to FDC, which are even more rich in CR1 and CR2 receptors, remains a mystery."

The close association of B cells, containing C3dg-opsonized immune complexes, with FDC can be mediated by both FcγRII and CR2 on the FDC. This association then allows transfer of the immune complex to the FDC for future presentation of intact antigen to specific B cells. FDC are not capable of internalizing immune complexes, and thus, when the transfer reaction occurs, the antigens will remain fixed on the surface of the FDC. It is well-established that antigens attached to FDC play an important role in stimulating antigen-specific B cells in order to produce an immune response, and the present invention provides a powerful means of insuring delivery of the antigen to the FDC. That is, antigens targeted to B cell CR2 with the anti-CR2 monoclonal antibody will ultimately be localized to FDC and thus act as potent immunogens.

In one embodiment of the present invention a composition and method is provided for enhancing an immune response to a target antigen. The composition comprises an antibody that specifically binds to CR2 and a target antigen that is linked to the CR2 antibody. The target antigen can be linked to the CR2 antibody either directly or indirectly. The target antigen can be selected from compounds that are unique to pathogenic organisms such as viruses or microorganisms or may include antigens specific for cancer cells, β-amyloid and toxins, such as those toxins produced by bacteria or viruses or to antigens associated with bacterial toxins including lipopolysaccharides as well as the toxins associated with anthrax, or to antigens associated with other microorganisms including parasites such as plasmodium falciparum, or other forms of the causative agents of malaria Typically, the antigen comprises a protein or carbohydrate epitope isolated from the pathogenic organism or targeted cell. In one embodiment the target antigen includes substances that, if present in large amounts, induce or aggravate disease states, such as viruses, pathogenic bacteria, whole cancer cells or toxins or metabolites produced by such cells. For example, the present invention can be used to rapidly produce a protective immune response against Anthrax Protective Antigen (APA), or against Anthrax Lethal Factor or Anthrax Edema Factor. For example, the anti-CR2 monoclonal antibody can be cross-linked with a monoclonal antibody specific for APA, and then the bispecific complex would be combined with APA, purified, and then used as an intravenous immmuogen.

In one embodiment, a composition, comprising a bi-specific complex, is provided for inducing or enhancing an immune response against a target antigen. More particularly, the bi-specific complex comprises a first portion and a second portion, wherein the first portion comprises an antibody directed to complement receptor 2 (CR2), and the second portion comprises the target antigen. The first and second portions of the bi-specific complex are linked to one another. In one embodiment the second portion comprises a linking moiety that is bound to both the first portion and the target antigen. Preferably the linking moiety is covalently bound to the first portion and can be selected from any of the standard linkers known to those skilled in the art. In one embodiment the linking moiety comprises a second antibody that is specific for the target antigen, wherein the second antibody is linked to the CR2 receptor antibody. The bi-specific antibody complexes of the present invention may further include CR2 bearing cells (such as B cells) and/or the target antigen already bound to the complex Alternatively, in one embodiment the second portion of the bi-specific complex target comprises an antigenic peptide sequence that is subsumed within the primary amino acid sequence of the CR2 receptor antibody (the first portion). In accordance with one embodiment, the CR2 receptor antibody is engineered to contain the target antigen within the primary amino acid sequence of the CR2 receptor antibody. In preferred embodiments the amino acid sequence of the CR2 receptor antibody is engineered to contain the target antigenic peptide at a location other than the constant fragment (Fc) portion responsible for interaction with Fc receptors. In one embodiment the target peptide antigenic sequence is located within the variable fragment (Fv) region of the CR2 receptor antibody, but does not prevent the CR2 receptor monoclonal antibody from binding to CR2.

In one embodiment the bispecific complex of the present invention is used to induce an immune response in an individual to a specific target antigen. In this embodiment the target antigen is linked to the bispecific complex and administered to the individual using standard techniques. The target antigen can be linked directly or indirectly to the monoclonal antibody specific for B cell CR2. For example the antibody specific for B cell CR2 can be directly attached to the antigen or attached through a linker. The linker can be any polymer, or in one preferred embodiment the linker comprises a second antibody that specifically binds to the target antigen. The bispecific complex is then introduced into an animal, and preferably by intravenous administration, in order to generate a robust immune response.

The complexes of the present invention can be used to prophylactically induce an immune response in a warm blooded vertebrate or in one embodiment the complexes are used to enhance an immune response to an antigen already present in the warm blooded vertebrate. In the latter embodiment, one method of inducing/enhancing an immune response to an antigen already present in the individual comprises the steps of administering to that individual a bispecific antibody complex comprising an antibody specific for CR2 linked to an antibody specific for the target antigen. Alternatively, the target antigen can be bound to the target-specific antibody in vitro prior to the administration of the complex to the individual. Furthermore, in accordance with one embodiment the complexes (with or without the target antigen bound) can be bound to B cells via CR2 in vitro before they are administered to the individual. For example, a small amount of blood can be extracted from the patient, and combined with the bi-specific antibody complex under sterile in vitro conditions and then reintroduced into the patient, preferably by intravenous administration using one or more injections. The antigenic compositions of the present invention may further comprise adjuvants, diluents, excipients, solubilizing agents, fillers as well as pharmaceutically acceptable carriers.

The key to the generation of the immune response is the expectation that antigens associated with B cell CR2 in the aforementioned constructs will be transferred to follicular dendritic cells (FDC) in the spleen and in the lymphatics. After such transfer, the antigens will be displayed, intact on the FDC, until they interact with B cells specific for the displayed antigen. This interaction will stimulate the B cell and ultimately lead to the generation of an effective humoral immune response.

The bispecific antibody complexes of the present invention can be prepared using standard techniques. The first step is to obtain a monoclonal antibody that is specific for CR2. This first monoclonal antibody is further modified to contain the antigen within the coding sequence of the CR2 antibody, or the target antigen is linked directly or indirectly to the CR2 antibody. In one embodiment, the method of preparing a modified CR2 antibody that contains the target antigen encoded within the antibody's primary sequence comprises the steps of isolating the gene encoding the CR2 antibody and recombinantly modifying the gene sequence to splice an antigenic peptide sequence into the coding region of the CR2 antibody.

Alternatively, the target antigen can be linked either directly or indirectly to the CR2 antibody through a linker. In one embodiment the antigen is linked indirectly to the CR2 antibody wherein the linker constitutes a second monoclonal antibody that specifically binds to the target antigen. In this embodiment the CR2 monoclonal antibody will be cross-linked to the second monoclonal antibody in a manner that does not interfere with either monoclonal antibody's ability to bind to their respective antigens. Cross-linking can be performed by any efficacious cross-linking method, as described in U.S. Pat. No. 4,676,980, the disclosure of which is incorporated herein. Additional details of the preparation of cross-linked bispecific monoclonal antibody complexes can be found in Lindorfer et al., Journal of Immunology, 167, 2240-2249 (2001). In one embodiment the cross-linked complexes of the present invention are prepared using N-succinimidyl 3-(2-pyridyldithio)propionate (SPDP) according to established, published procedures. For details as to this procedure, see, e.g., Karpovsky et al, J. Exp. Med. 160, 1686-1701 (1984); Perez et al, Nature, 316, 354-356 (1985) or Titus et al, Journal of Immunology, 139, 3153-3158 (1987).

In accordance with one embodiment an antigenic composition is prepared for inducing or enhancing an immune response in a warm blooded vertebrate wherein the composition comprises a mAb specific for CR2 cross linked-with a mAb specific for the target antigen. This second mAb can be made in mice by conventional immunization and will be bound to the target antigen prior to administration to the animal/human. A composition comprising the bispecific reagent (preferably with the target antigen bound) and a pharmaceutically acceptable carrier can then be administered to an animal or human to induce an immune response to the bound target antigen. In one embodiment the bispecific reagent (with a bound target antigen) is first contacted with CR2 bearing cells (such as B cells), to bind the immunogen to the B cells, and then the complex is infused into the animal/human to be vaccinated.

The compositions of the present invention can be administered using any of the known routes of administration, including, intravenous, intramuscle, intraparenteral, or subcutaneous injection. However, intravenous administration is preferred.

Intrasplenic injections of the osponized B cells may well provide a particularly advantageous route for generating a robust immune response in mice for the purpose of mAb production. In the embodiment where the bispecific reagent is contacted with B cells prior to administration to the individual, all of the immunogen should be bound to the B cells initially. Therefore the complexes should provoke a very effective immune response at relatively low inputs. The use of ex-vivo loaded dendritic cells for vaccines is a very active area of investigation, but it is anticipated that the present method that utilizes B cells will be far more effective. This anticipated enhanced efficacy derives from both the ability to insure substantial and avid binding of the immunogen to the B cells, and because once the complexes are infused back into the animal/human, they will insure proper delivery to germinal centers in the lymphatics where they will transfer the immunogen to FDC and/or macrophages. It is anticipated that the B cell containing the bound immunogen/immune complex will localize to FDC in a variety of body compartments including the spleen, and lymphatics.

In another embodiment the bispecific monoclonal antibody complexes of the present invention can be used as a therapeutic agent for targeting pathogens present in the bloodstream or the lymphatic system and enhancing an immune response against such pathogens. In this embodiment the bispecific monoclonal antibody complex comprises a monoclonal antibody specific for CR2 cross linked with a monoclonal antibody specific for a target pathogen antigen. In this case either the freely-soluble bispecific complex will be administered to the individual, and it will naturally seek out and bind to B cells, or the B cells can be opsonized ex-vivo and then administered. The pathogen will bind to the bispecific complex on the B cells, and then be transferred to FDC for presentation to the immune system. Accordingly, a method for stimulating an immune response against a target antigen comprises the step of administering a bispecific antibody complex, comprising an antibody specific for CR2 linked to an antibody specific for the target antigen, wherein the target antigen is bound to the antibody specific for the target antigen.

It is also anticipated that B cells containing the bound immunogen/immune complex will localize to acceptor macrophages in a variety of body compartments including the spleen, where the complex will be taken up by macrophages in an Fc receptor mediated reaction. In accordance with one embodiment of the invention this mechanism is utilized for enhancing the clearance of undesirable material from the bloodstream of an individual. The method comprises the step of administering, preferably by intravenous injection, to the individual a composition comprising the bi-specific antibody complex of the present invention. The complex comprises a first antibody linked to a second antibody, wherein the first antibody specifically binds to CR2, and the second antibody specifically binds to a unique epitope present on the undesirable material. In preferred embodiments the antibodies are monoclonal antibodies. The administered complexes will specifically bind to the undesirable material as well as to CR2 present on B cells. The entire complex will then be cleared from the circulation of human and non-human primates through the transfer reaction, without clearance of the B cells themselves.

The undesirable material to be cleared from the individual's bloodstream may include any compound that is related to a pathogenic organism, including toxins or unique antigenic determinants of such organisms, or related to a disease state (eg amyloid plaques in Alzheimer's disease or cancer cell determinants) or a compound that is only detrimental when accumulated in high amounts. The complexes of the present invention can be used to substantially reduce the concentration of such materials. More particularly, in one embodiment the undesirable material is selected from the group consisting of neoplastic cell specific antigen, a pathogenic bacteria or virus specific antigen, low density lipoprotein and β-amyloid.

In one embodiment the bispecific mAb complexes comprising an anti-CR2 mAb crosslinked with a target antigen mAb is administered to a patient without having the antigen bound to the complex. In this manner the bispecific antibody complexes provide a powerful therapeutic device for targeting pathogens in the lymphatics as well as in the bloodstream of a patient. In accordance with one embodiment a bispecific mAb complex comprising an anti-CR2 mAb crosslinked with a target antigen mAb is used to treat a disease or infection. In this embodiment, the complexes will be administered to the patient, wherein upon administration, the complex binds to the target antigen (such as a pathogen, tumor cell or toxin antigen) present in the bloodstream or lymphatic system, and allows for the removal of the antigen through the body's natural clearance system.

It is well documented that in AIDS patients a fraction of HIV contains fragments of C3dg and is apparently held on CR2 of follicular dendritic cells in the lymphatic system. HIV has also been demonstrated to be bound to CR2 of B lymphocytes as a consequence of complement activation, and several lines of evidence indicate that this form of HIV on B cells can infect T cells as well. Use of the bispecific reagents will insure that HIV bound to either follicular dendritic cells or B cells will be properly transferred to macrophages for destruction, because the therapeutic device will provide the crucial Fc regions of the mAbs which must interact with Fc receptors of the macrophage to insure proper transfer and pathogen destruction.

In accordance with one embodiment a method for treating a warm blooded vertebrate suffering from a pathogenic disease (including viral or microbial infections), septic shock, or cancer is provided. As used herein, the term "treating" includes alleviating the symptoms associated with a specific disorder or condition and/or preventing or eliminating said symptoms or the cause of the symptoms. The method comprises the steps of administering a bispecific monoclonal antibody complex to a warm blooded vertebrate in need of such therapy, wherein the bispecific monoclonal antibody complex comprises a monoclonal antibody specific for CR2 crosslinked with pathogen/cancer specific monoclonal antibody.

In one embodiment the monoclonal antibody is a mouse IgG or a human IgG, in order to insure interaction with the Fc receptor (FcγRII) on the FDC. The transfer of pathogenic antigen/bispecific monoclonal antibody complex from the B cell to an acceptor FDC cell depends upon immune complex recognition by Fc receptors. Based on the effects of specific monoclonal antibodies in blocking the transfer reaction from erythrocyte CR1, the engagement of FcγRII in particular, is believed to play an important role in the transfer reaction. Accordingly, it is anticipated that the bispecific monoclonal antibody complexes used to target pathogens in the body will work most effectively (i.e. provide the most efficient and rapid transfer) if they are constructed with monoclonal antibodies which effectively engage FcγRII.

When the bispecific monoclonal antibody complexes are injected into the circulation of a warm blooded vertebrate (and more particularly a human or warm-blooded vertebrate animal), the bispecific monoclonal antibody complex will readily bind to B cells via the anti-CR2 monoclonal antibody at a high percentage and in agreement with the number of CR2 sites on the B cells. At approximately the same rate, the bispecific monoclonal antibody complex will bind to the target antigen via the anti-pathogen/cancer specific monoclonal antibody. The pathogen bound bispecific monoclonal antibody complexes, initially bound to B cells, will be rapidly (within 24 hours) localized to FDC for initiation of a robust immune response or they will be transferred to a macrophage for removal from the body through the body's natural clearance system. Accordingly, one aspect of the present invention relates to the use of the bispecific monoclonal antibody complexes to target pathogens in the bloodstream or the lymphatic system of a human, wherein the bispecific monoclonal antibody complex comprises a human IgG monoclonal antibody for at least the anti-pathogen monoclonal antibody.

In one embodiment the method for treating a warm blooded vertebrate suffering from a pathogenic disease (including viral or microbial infections), septic shock, or cancer comprising the step of administering a bispecific monoclonal antibody complex of the present invention. In one embodiment the method of treating further comprises the step of contacting the complexes with CR2 bearing cells (e.g. B cells) before the complexes are administered to the patient. For example, B cells can be removed and isolated from the individual to be treated and contacted with the bispecific monoclonal antibody complexes ex vivo. Alternatively, the step of contacting the bispecific complex with CR2 bearing cells can be conducted by obtaining a blood sample from the vertebrate to be treated, and mixing the bispecific complex with the blood sample. After incubating the B cell/bispecific monoclonal antibody mixture for a time sufficient to allow the complexes to bind to the B cells, the complexed B cells are reintroduced into the patient. The complexed B cells will then circulate through the bloodstream and lymphatic system and bind any free pathogenic/cancer antigens, thus immobilizing the antigen on the B cell, and subsequently transferring the antigen to FDC or a macrophage in accordance with the transfer reaction.

When the compositions of the present invention are used to treat a warm blooded vertebrate species suffering from a pathogenic disease, septic shock, or cancer the compositions comprising the bispecific complex can be administered using any of the known routes of administration, including, intravenous, intramuscle, intraparenteral, or subcutaneous. In one embodiment the bispecific complexes are administered locally to the area in need of treatment. For example, when treating cancer a bispecific complex comprising a monoclonal antibody for CR2 crosslinked to a monoclonal antibody specific for a tumor antigen can be administered locally using standard techniques including by injection, local infusion during surgery or by means of an implant.

The amount of bispecific monoclonal antibody complexes to be administered to the warm blooded vertebrate is determined based on the in vivo B cell concentration and the number of CR2 epitope sites recognized by the anti-CR2 monoclonal antibodies per B cell. In accordance with one embodiment, combinations of bispecific monoclonal antibody complexes that contain monoclonal antibodies that bind to separate and non-competing sites on CR2 will be used. Therefore, a "cocktail" containing a mixture of two or more bispecific monoclonal antibody complexes that differ only in the specificity of the anti-CR2 monoclonal antibody will ensure that an amount of bispecific monoclonal antibody complex can be administered to effectively bind substantially all of the target pathogenic/cancer antigen without overloading the CR2 sites on the B cells. Furthermore, in one embodiment the bispecific monoclonal antibody complex cocktail comprises multiple bispecific complexes, wherein the complexes differ from one another based on the CR2 specific epitope the individual CR2 antibodies bind. In another embodiment, each of the multiple bispecific complexes contain different combinations of monoclonal antibody specificities, such that the respective CR2 and pathogenic/cancer monoclonal antibodies each bind to separate and non-competing sites with their target antigen.

The present invention is also directed to recombinant monoclonal antibodies wherein variable region framework codons are exchanged for human antibody variable region framework codons while preserving the CDR sequences to "humanize" the antibody reagents and bispecific complexes and thus further lessen the likelihood of generating immune responses to the complexes themselves in human patients. In addition, the native antibody sequences can be modified, using standard techniques known to those skilled in the art, to make the gene more suitable for expression in prokaryotic cells. For example one or more codons of the gene encoding the antibody can be exchanged for codon sequences more commonly used by bacteria. It is anticipated that the removal of infrequent bacterial codons will allow the miniantibody to be expressed in *E. coli* at higher concentrations.

EXAMPLE 1

Immune Complexes bound to erythrocytes via complement opsonization are effectively transferred to acceptor macrophages.

Applicants first examined complement-dependent binding of a bacteriophage (PhiX174) immune complex (IC), comprising the PhiX174 bacteriophage bound to an antibody specific for that bacteriophage (the PhiX174/anti-PhiX174 IC), to erythrocyte CR1 and Raji cell CR2 under various conditions (Table II). Binding of immune complexes to either cell type required normal human serum (NHS), and if complement activity was abrogated by heat inactivation or addition of EDTA, no binding was detected. If erythrocytes or Raji cells were pretreated with monoclonal antibodies specific for the ligand binding site on CR1 or CR2, respectively, immune complex binding was eliminated. Experiments with monoclonal antibody 1H8, specific for C3dg, confirmed that this complement fragment was associated with Raji cells with bound complement opsonized immune complexes. Treatment of these cells with an anti-CR2 monoclonal antibody (FE8) led to release of >80% of both the bound immune complexes and C3dg.

TABLE II

Binding of PhiX174/anti-PhiX174 monoclonal antibody immune complexes to Human Erythrocytes or Raji cells Requires Complement

| Condition | Binding[1] to: | |
|---|---|---|
| | Human Erythrocyte | Raji Cells |
| Serum | + | + |
| Media | − | − |
| Heat inactivated serum | − | − |
| Serum EDTA | − | − |
| Serum; cells pre-treated with cognate blocking anti-CR monoclonal antibody[2] | − | − |

[1]Binding assessed by RIA and/or flow cytometry.
[2]Human Erythrocytes: monoclonal antibody 1B4. Raji cells: monoclonal antibody FE8. 10 ug/ml.

Figure 1A:
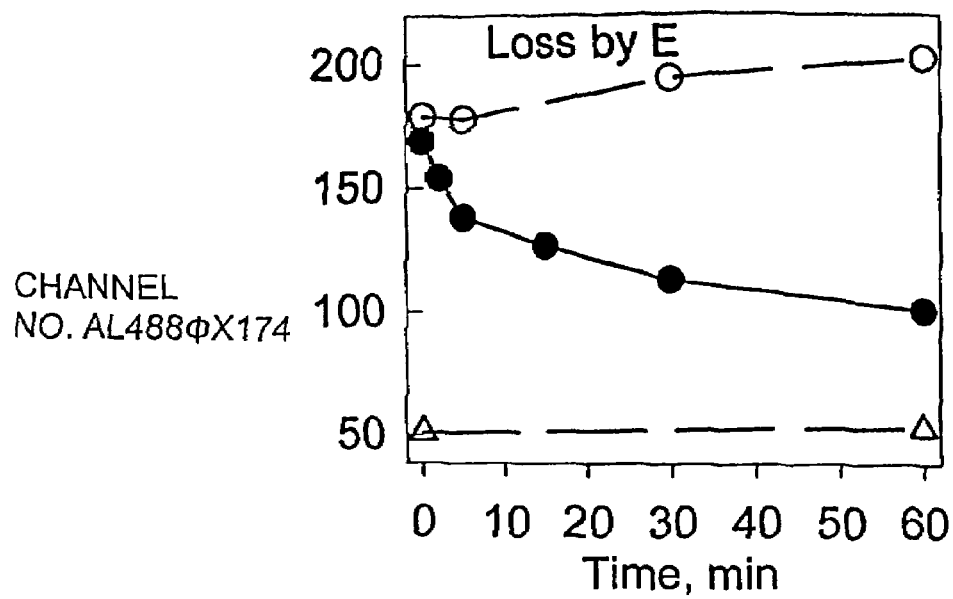
FIGS. 1A & B. Flow cytometry (fluorescence activated cell sorting) was used to measure the transfer of complement opsonized immune complexes (C3dg-IC), bound to erythrocyte CR1 by immune adherence, to THP-1 cells (an acceptor macrophage lineage). After 60 min, 76% of the immune complexes were removed from erythrocytes incubated with THP-1 cells. Symbols: Filled circles, immune complex opsonized erythrocyte and THP-1 cells; open circles, immune complex opsonized erythrocyte only; open triangles, naïve erythrocyte; open squares, THP-1 cells only.
Figure 1B:
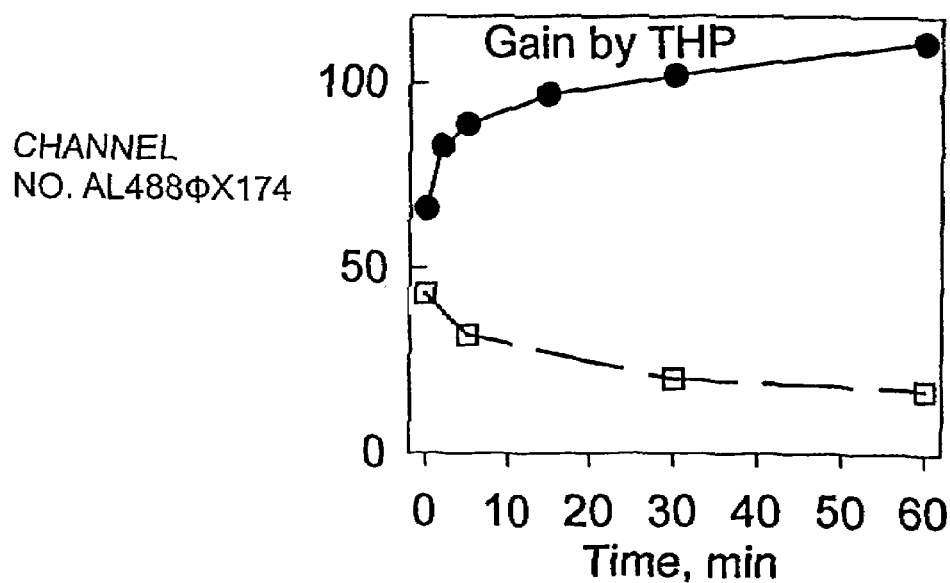

For purposes of comparison transfer of complement opsonized immune complexes from erythrocytes to THP-1 cells was investigated. PhiX174 was labeled with A1488 (a fluorescent marker) to allow direct detection of the immune complex, and THP-1 cells were labeled with PKH26 (a fluorescent marker) to distinguish them from donor cells. The abbreviation A1488-PhiX174 represents the PhiX174 bacteriophage labeled with the A1488 marker. Complement opsonized immune complexes bound to erythrocyte CR1 are stable in media for 60 min (FIG. 1A, open circles). However, when combined with THP-1 cells, erythrocyte bound immune complexes were rapidly released and transferred to THP-1 cells (FIG. 1A,B, filled circles). This transfer reaction was also followed by fluorescence microscopy.

EXAMPLE 2

Immune Complexes bound to Raji cells via complement opsonization are effectively transferred to acceptor macrophages.

Similar experiments were performed with Raji cells as donor cells.

Figure 2C:
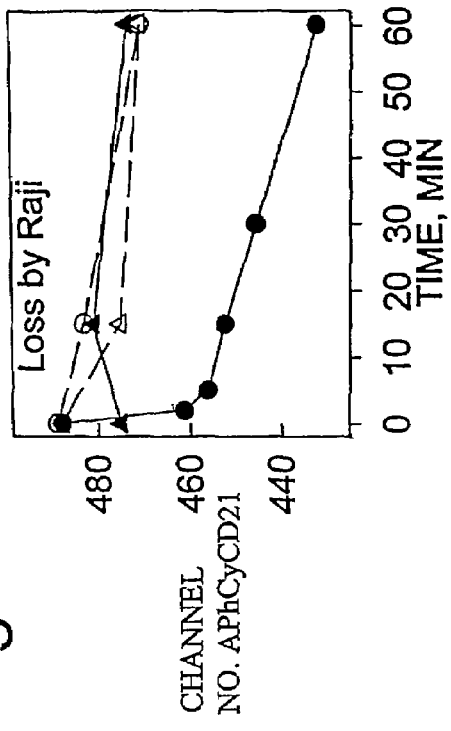
FIG. 2A-D. Flow cytometry (fluorescence activated cell sorting) was used to measure the simultaneous transfer of complement opsonized immune complexes (C3dg-IC), bound to CR2 by immune adherence, and CR2 from Raji cells (a B cell lineage) to THP-1 cells. APhCy represents the fluorophore, allophycocyanin and a complete list of the cell transfer substrates and the probes used to detect the substrates is provided in Table I. After 30 min, >90% of the immune complexes and 38% of CR2 were removed from Raji cells incubated with THP-1 cells, compared to 13% loss of immune complexes and 14% loss of CR2 from Raji cells incubated alone. Symbols: Filled circles, immune complex (C3dg/A1488-PhiX174) opsonized Raji cells in the presence of THP-1 cells; open circles, immune complex opsonized Raji cells only; filled triangles, naïve Raji plus THP-1 cells; open triangles, naïve Raji cells only; open squares, TBP-1 cells only.
Figure 2D:
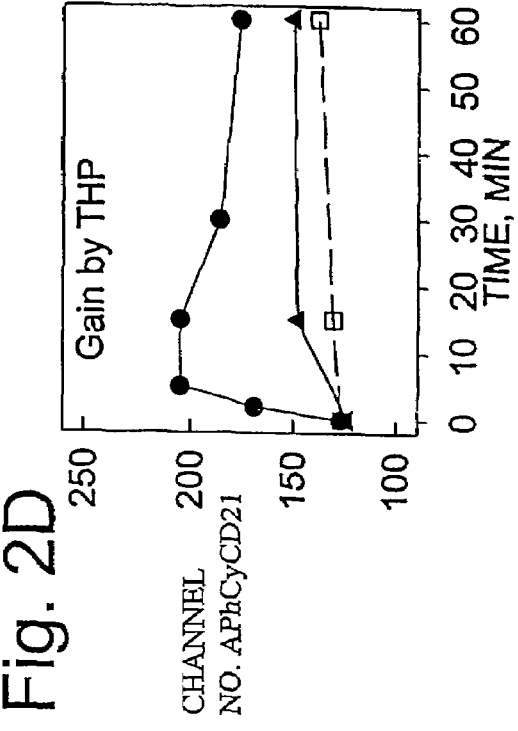
Figure 2A:
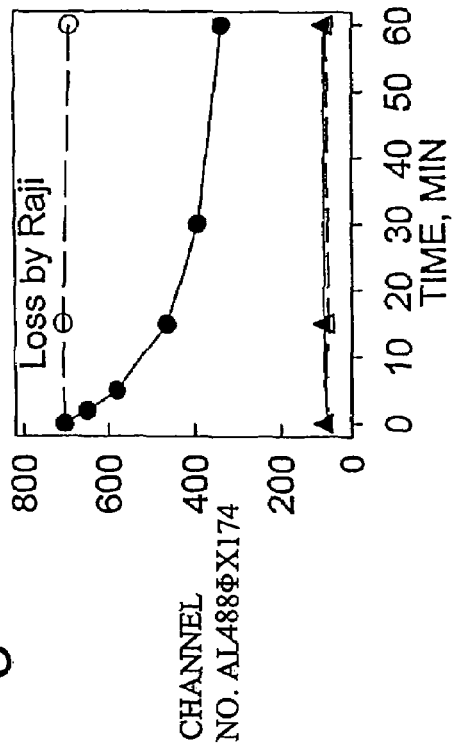

When the A1488 PhiX174/anti-PhiX174 immune complex was incubated in NHS for 30 min at 37C, stable binding of A1488 PhiX174 to Raji cells was detectable by flow cytometry (FIG. 2A, open circles). However, in the presence of TBP-1 cells, the immune complexes were rapidly transferred (FIG. 2A,B, filled circles). We probed the cell mixtures for CR2 (using an anti-CR2 antibody that is fluorescently labeled: APhCy CD21) and found, as previously observed by others (Fremeaux-Bacchi et al., European Journal of Immunology, 26, 1497-1503 (1996), that Raji cells display a slow rate of spontaneous loss of CR2 when incubated alone (FIG. 2C, open circles and triangles, respectively).

Figure 2B:
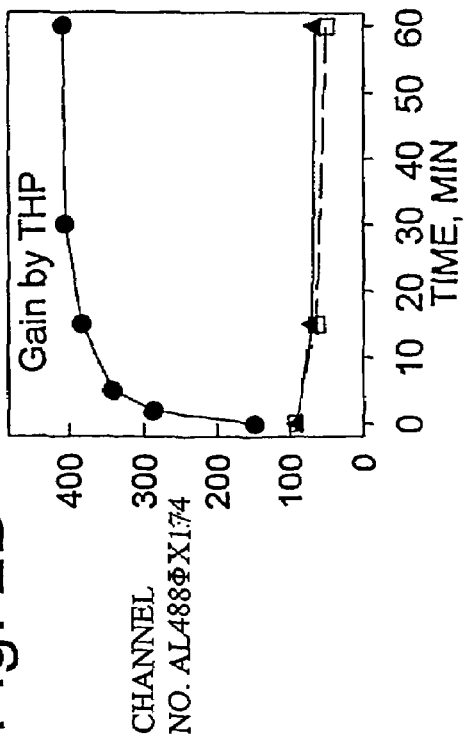
Figure 3A:
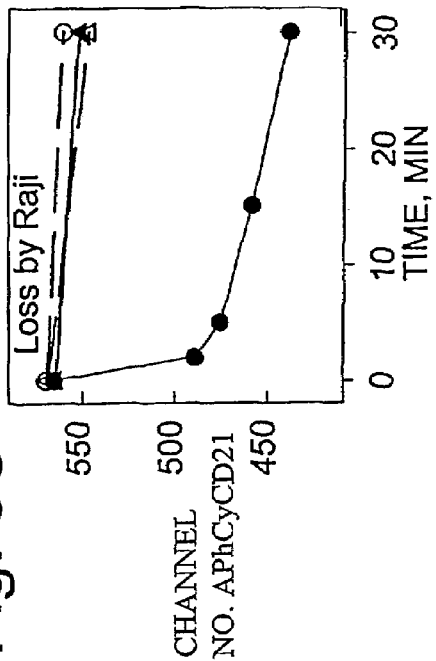
Figure 3B:
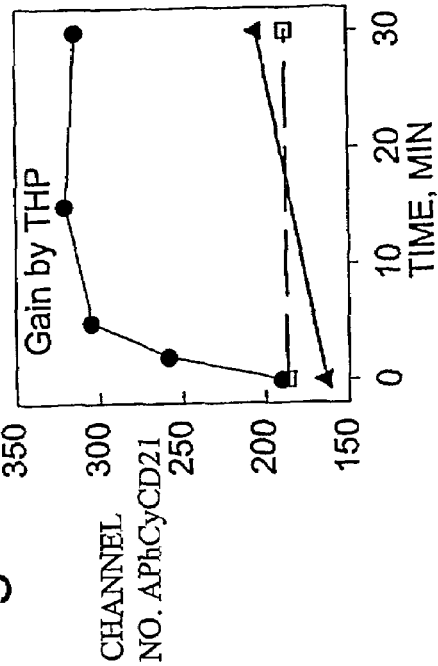
Figure 3C:
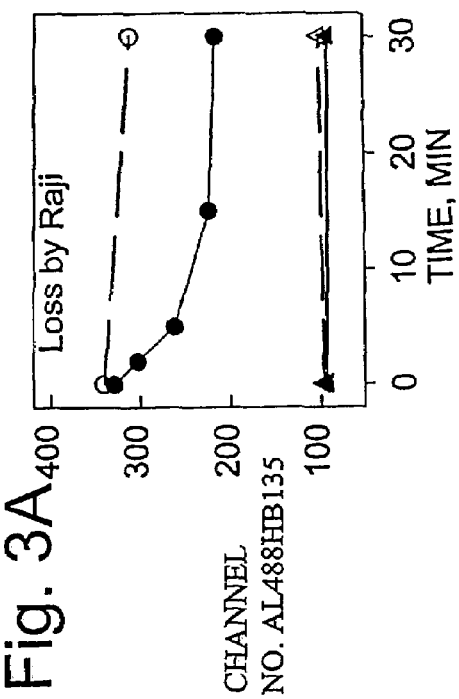
Figure 3D:
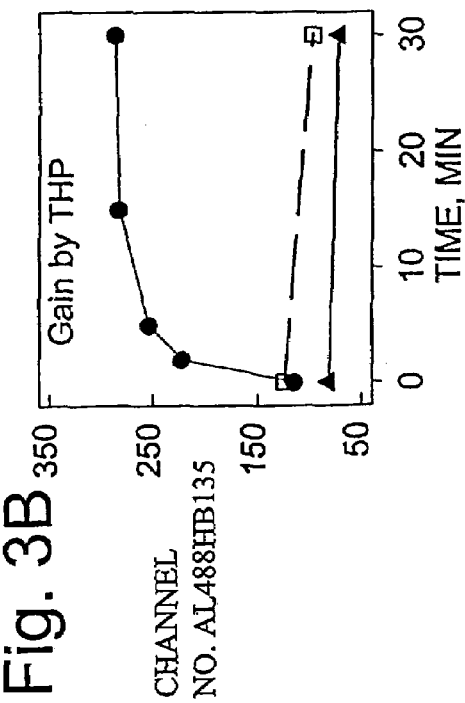

Co-incubation with THP-1 cells greatly increased the rate of loss of CR2 from Raji cells containing bound immune complexes, but not from naïve Raji cells (FIG. 2C, filled circles compared to filled triangles). Both the intrinsically labeled A1488 immune complexes (FIG. 2B) and CR2, as indicated by the extrinsic anti-CR2 probe (APhCy CD21; see FIG. 2D), were transferred to TEP-1 cells. In contrast to the behavior of the intrinsic A1488 immune complex label, the extrinsic signal rose rapidly and then slowly declined to 70% of its peak value (FIG. 2D). Thus both immune complexes and CR2 were removed from the donor cell and transferred to the acceptor cell with very similar kinetics. The subsequent decrease in magnitude of extrinsic signal attributable to CR2 on TBP-1 cells may reflect either internalization by or release from the THP-1 cells. We also followed transfer of bound immune complexes from Raji cells to THP-1 cells by fluorescence microscopy.

EXAMPLE 3

IgG and Immune Complexes bound to Raji cells via an anti-CR2 monoclonal antibody are effectively transferred to acceptor macrophages, and the reaction requires FCR (Fc receptors).

To extend this work to a complement-independent paradigm, Raji cells were opsonized by ligation with the mouse anti-CR2 monoclonal antibody HB135. As shown in FIG. 3, both CR2 and the anti-CR2 monoclonal antibody were transferred from Raji cells to THP-1 cells; the intrinsic (HB135 antibody labeled with A1488) and extrinsic probes (APhCy CD21; a fluorescently labeled anti-CR2 antibody) demonstrated similar kinetics of transfer to THP-1 cells. To more closely simulate B cell bound immune complexes in the absence of complement, Raji cells previously incubated with A1488 labeled HB135 or unlabeled HB135 were further reacted with either rabbit anti-mouse IgG or A1488 labeled rabbit anti-mouse IgG (FIGS. 4 and 5, respectively). Both immune complexes were examined in the transfer reaction and in each case the intrinsic A1488 label (monoclonal antibody HB135, FIG. 4C,D, or rabbit anti-mouse IgG, FIG. 5C,D) was transferred at a rate similar to that observed for the transfer of monoclonal antibody HB135 (FIG. 3). After transfer, cell mixtures were probed with A1633 goat anti-rabbit IgG (FIGS. 4A,B, 5A,B) or APhCy anti-CR2 (FIGS. 4E,F, 5E,F) to monitor the two other components of the complex. As we observed for immune complexes prepared with complement, both extrinsic probes showed an initial rapid rise in the THP-1 associated signal, followed by a decrease over the next 20 min.

To determine if the Fc portion of IgG was necessary for the transfer reaction, Raji cells were opsonized with the F(ab)'$_2$ fragment of monoclonal antibody HB135 and the transfer rate was compared with that of cells reacted with intact monoclonal antibody HB135 (see FIG. 6; ♦ represents Raji cells opsonized with the the HB135 F(ab)'$_2$ and ● represents Raji cells opsonized with the intact HB135 mAb). As demonstrated previously (FIG. 3), intact monoclonal antibody HB135 and associated CR2 were simultaneously transferred from the Raji cell to the acceptor cell. However, for cells opsonized with the F(ab)'$_2$ fragment of monoclonal antibody HB135, neither the monoclonal antibody fragment nor CR2 were removed from the donor cell or taken up by THP-1 cells. Thus, the Fc portion of the substrate appears to be necessary for transfer.

To further examine the possible role of Fc receptors in the transfer reaction, THP-1 cells were pre-incubated with human IgG. This step blocked transfer of an anti-CR2 monoclonal antibody/rabbit anti-mouse IgG immune complex from Raji cells (FIG. 7). As shown by the filled triangles (FIG. 7A,C), loss of both A1488 rabbit anti-mouse IgG and CR2 from the Raji cells was reduced, and the rate of loss was similar to the rates observed in the absence of TBP-1 cells. Moreover, the IgG-treated THP-1 cells did not take up either A1488 rabbit anti-mouse IgG or CR2 (FIG. 7B,D).

EXAMPLE 4

Immune Complexes bound to Monkey B cells via an anti-CR2 monoclonal antibody are effectively cleared from the circulation and localized to the spleen.

In vitro calibration studies with whole blood from 4 cynomolgus monkeys established that the anti-human CR2 monoclonal antibody HB135 (but not an isotype control) recognizes CR2 on monkey B cells; in addition, A1633 rabbit anti-mouse IgG only bound to B cells after pre-treatment with monoclonal antibody HB135. Typically 70% of monkey B cells (identified as CD20 and CD45 positive) were identified as being CR2 positive. A study was performed on a monkey that had a low titer of circulating anti-mouse IgG, due to an i.v. infusion of mouse IgG one year earlier. A1488 HB135 was infused i.v. as a bolus at a dose of 50 ug/kg. The A1488 HB135 bound rapidly (within 2 min) to circulating B cells (FIG. 8A,C), and a fraction of cell bound monoclonal antibody was cleared within 30 min. ELISA measurements confirmed a low level of anti-mouse IgG in the pre-infusion samples which was eliminated 30 min after infusion of A1488 monoclonal antibody HB135.

Figure 8A:
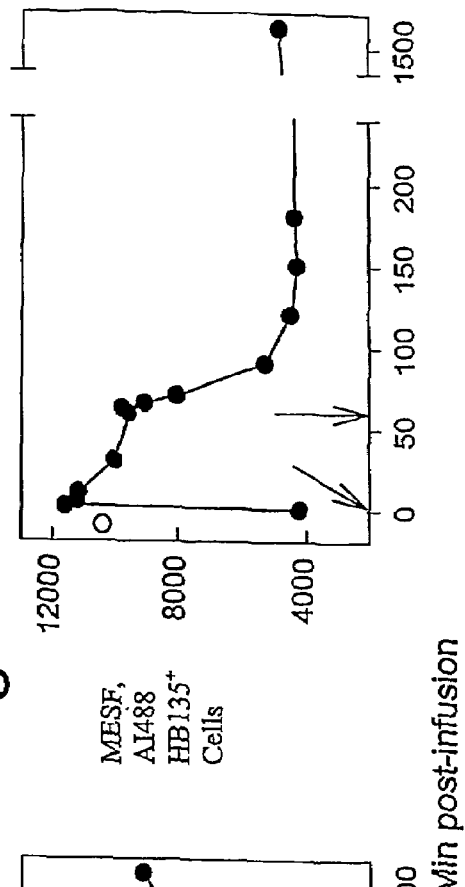
Figure 8B:
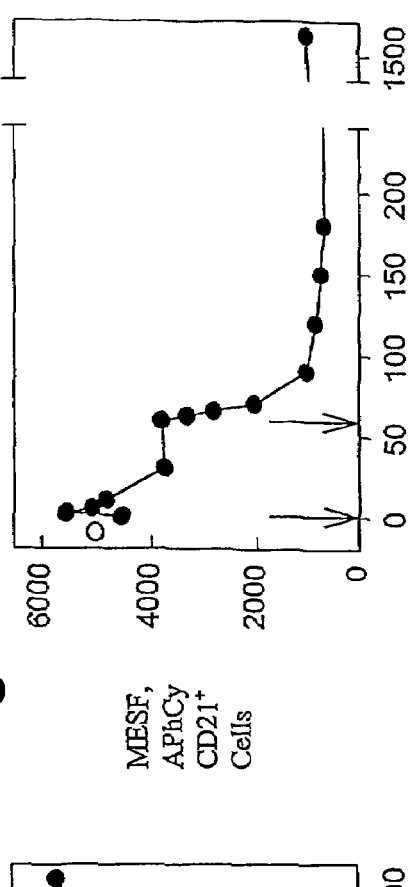
Figure 8C:
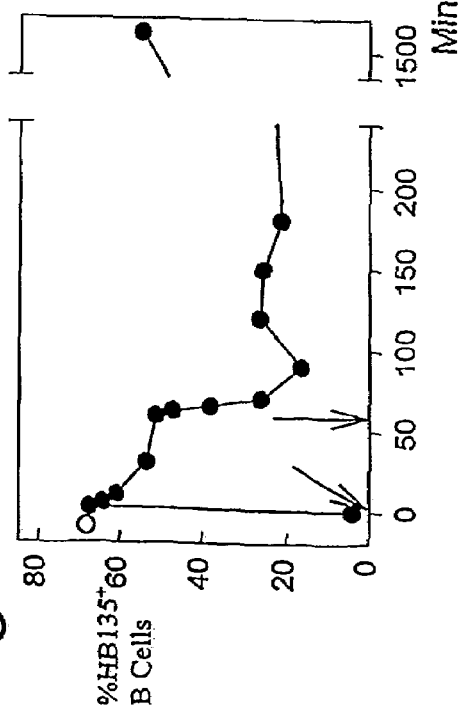
Figure 8D:
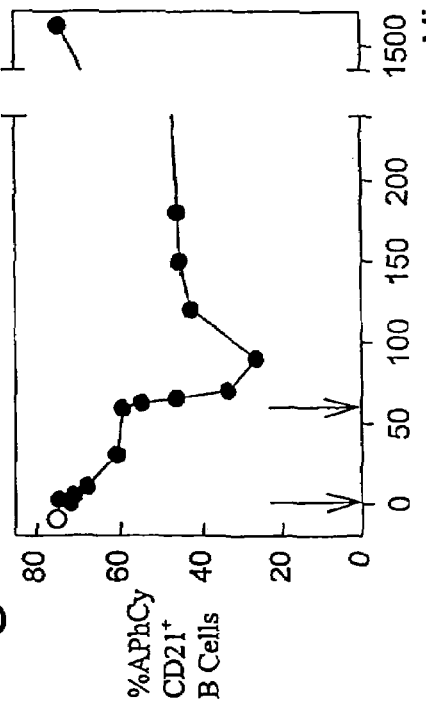

Rabbit anti-mouse IgG (100 ug/kg) was infused at the 60 min mark (FIG. 8, second arrow), and it immediately bound to the mouse monoclonal antibody already on the B cells as demonstrated by an increase in the A1633 goat anti-rabbit signal (MESF=1520, 2 min after infusion; background 450 before infusion). Shortly after this second infusion, a fraction of the CR2 positive B cells (defined by either A1488 HB135 or the APhCy anti-CD21 probe) were temporarily removed from the bloodstream (FIG. 8A,B) and the remaining CR2 positive B cells underwent a rapid loss of both bound A1488 labeled BB 3135 as well as the CD21 epitope (FIG. 8C,D). At the 24 h point the fraction of CR2 positive B cells found in the bloodstream returned to the pre-infusion values (FIG. 8A,B); however, the majority of the B cell bound monoclonal antibody HB135 demonstrable at 60 min had been removed from the cells (FIG. 8C), coincident with the loss of the majority of the CD21 epitope (FIG. 8D). In addition, the rabbit IgG bound to the B cells at 60 min was also cleared (final MESF=445). Both spleen and liver sections were examined for localized A1488 monoclonal antibody HB13135 and rabbit IgG, and both proteins were clearly demonstrable and co-localized in the spleen, but were not detectable in the liver. A similar experiment (but only out to 3 h) was performed on another cynomolgus monkey and the same patterns of B cell binding, sequestration and clearance of bound ligands and CR2 was observed.

The in vitro studies, as well as the findings in the primate model, provide substantial evidence supporting the basic tenets of the B cell transfer reaction. Based on this data applicants believe transfer of immune complexes from B cells to FDC is a required step in the normal processing of antigens by antibodies and complement during the maturation of the immune response. The present invention allows for the very effective and specific focusing of antigens into the B cell to FDC transfer pathway, and will therefore leads to the generation of a wide variety of more effective vaccines for multiple targets.

The invention claimed is:

1. A method of enhancing an in vivo immune response in a warm blooded vertebrate, to a target antigen, said method comprising the step of injecting intravenously into said warm blooded vertebrate a bi-specific complex, wherein said complex comprises a first antibody that comprises an Fc portion, and a second portion, wherein said first antibody specifically binds to complement receptor 2, and said second portion comprises a target antigen, wherein the first antibody and the second portion are linked to one another, and further wherein when said complex is injected intravenously into said warm blooded vertebrate, said complex delivers said target antigen intact to follicular dendritic cells in the spleen.

2. The method of claim 1 wherein said second portion comprises a second antibody.

3. The method of claim 1 wherein said second portion comprises a second antibody that specifically binds said target antigen, said second antibody comprising an Fc portion, wherein said second antibody is linked to the first antibody and complexed with its target antigen.

4. The method of claim 1 wherein said second portion comprises a linking moiety that is bound to both the first antibody and the target antigen.

5. The method of claim 4 wherein the target antigen is an antigen displayed by a cancer cell.

6. The method of claim 1 wherein the target antigen is an antigen displayed by a cancer cell.

7. The method of claim 1 wherein two or more complexes are injected into said warm blooded vertebrate wherein said first antibody of the complexes each bind to a different non-competing site on the complement receptor 2.

8. A bi-specific complex comprising a first antibody that comprises an Fc portion, and a second portion, wherein said first antibody is linked to the second portion, and said first antibody specifically binds to complement receptor 2, said second portion comprises a cancer cell antigen.

9. The bi-specific complex of claim 8 wherein said second portion comprises a second antibody.

10. The bi-specific complex of claim 8 wherein said second portion comprises a second antibody comprising an Fc portion, wherein said second antibody specifically binds said cancer cell antigen, is linked to the first antibody, and is complexed with said cancer cell antigen.

11. The bi-specific complex of claim 8 wherein said second portion comprises a linking moiety that is bound to both the first antibody and the cancer cell antigen.

12. A bi-specific complex cocktail comprising a plurality of different bi-specific complexes, each of said different bispecific complexes comprising a first antibody that comprises an Fc portion, and a second portion, wherein said first antibody is linked to the second portion, said first antibody specifically binds to complement receptor 2, and said second portion comprises a target antigen.

13. The bi-specific complex cocktail of claim 12 wherein each of said different bi-specific complexes differ from one another based on the specificity of the first antibody, wherein the first antibody of each different bi-specific complex binds to a separate and non-competing site on complement receptor 2.

14. The bi-specific complex of claim 13 wherein said second portion comprises a linking moiety that is bound to both the first antibody and the target antigen.

15. The bi-specific complex of claim 12 wherein said second portion comprises a second antibody that specifically binds said target antigen, wherein each of said different bi-specific complexes differ from one another based on the specificity of said second antibody, wherein the second antibody of each different bi-specific complex binds to a separate and non-competing site on said target antigen.

* * * * *